(12) United States Patent
Goto et al.

(10) Patent No.: US 6,262,227 B1
(45) Date of Patent: Jul. 17, 2001

(54) PROCESS FOR PRODUCING A CATIONIC POLYMER

(75) Inventors: Takeshi Goto, Ryugasaki; Yoshinobu Higashi, Ushiku; Tokihiro Yokoi, Himeji; Takashi Fujisawa, Suita, all of (JP)

(73) Assignees: Hisamitsu Pharmaceutical Co., Inc., Tosu; Nippon Shokubai Co., Ltd., Osaka, both of (JP)

( * ) Notice: Subject to any disclaimer, the term of this patent is extended or adjusted under 35 U.S.C. 154(b) by 0 days.

(21) Appl. No.: 09/543,351

(22) Filed: Apr. 5, 2000

Related U.S. Application Data

(63) Continuation of application No. PCT/JP99/04210, filed on Aug. 4, 1999.

(30) Foreign Application Priority Data

Aug. 5, 1998 (JP) .................................................. 10-222056

(51) Int. Cl.$^7$ .................................................. C08F 283/00
(52) U.S. Cl. .................................................. 528/502
(58) Field of Search .................................................. 528/502

(56) References Cited

U.S. PATENT DOCUMENTS 5,665,348  9/1997  Okayama et al. ................ 424/78.35

FOREIGN PATENT DOCUMENTS

| 9-202732 | 8/1997 | (JP) . |
| 10-60010 | 3/1998 | (JP) . |
| 10-114661 | 5/1998 | (JP) . |
| WO 95/34588 | 12/1995 | (WO) . |
| WO 98/43653 | 10/1998 | (WO) . |

*Primary Examiner*—Terressa M. Boykin
(74) *Attorney, Agent, or Firm*—Oblon, Spivak, McClelland, Maier & Neustadt, P.C.

(57) ABSTRACT

A process produces a cationic polymer having a cholesterol-lowering activity, which the process includes a step for subjecting a water-soluble monomer component essentially including a cationic monomer to aqueous polymerization so that the viscosity of a polymerization reaction solution is 1,000 cps or more and less than 300,000 cps at the point of time when a polymerization rate reaches 90%, a step for continuing the polymerization until the polymerization rate exceeds 95%, a step for ultrafiltrating the obtained aqueous polymer, a step for concentrating the ultrafiltration treated solution under reduced pressure at a temperature of the solution lower than 100° C., and a step for drying the concentrated solution under a specific condition. The production process can attain both the safety as a drug and a satisfactory production efficiency.

10 Claims, No Drawings

PROCESS FOR PRODUCING A CATIONIC POLYMER

This application is a Continuation of International Application No. PCT/JP99/04210 Filed on Aug. 4, 1999.

BACKGROUND OF THE INVENTION

1. Field of the Invention

The present invention relates to a process for producing a specific cationic polymer having a marked activity as a cholesterol-lowering drug and relates to a production process capable of achieving both properties of the safety as a drug and a satisfactory production efficiency.

2. Description of the Prior Art

Cationic polymers have cationic groups that can be ionized in water to yield cation. Typical examples of such cationic polymers include a polymer having quaternary ammonium salt groups or amino groups, which are used in the fields of, for example, ion-exchange resins, adsorbents, and flocculants. Cationic polymers having efficacy as drugs have been found in recent years, and expectations are made for developing new applications of these polymers. Especially, a cationic polymer having a unit shown by the following formula (III) has been found to lower a blood cholesterol level (PCT International Publication No. WO93/13781).

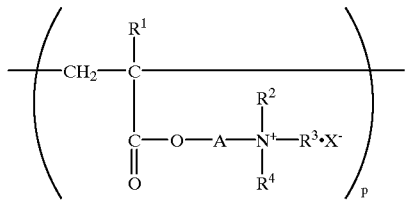

(wherein $R^1$ is H or a methyl group; $R^2$, $R^3$, and $R^4$ are each independently H, an alkyl group, or an aralkyl group; A is an alkylene group; $X^-$ is a counter anion; and p is an average polymerization degree.)

When such cationic polymers and other polymers are used as drugs, the most problematic matter is the existence of impurities such as low molecular weight polymer, unreacted monomer, and the like. This is because such low molecular weight polymer and unreacted monomers act as toxic substances or foreign substances in vivo and may cause adverse drug reactions, even though the polymers themselves have efficacies as drugs. A principle in the formation of such polymers does not allow them to have a single molecular weight but always render them polydisperse, and low molecular weight polymer and unreacted monomers are therefore inevitably formed. Accordingly, these low molecular weight polymer and unreacted monomers must be removed.

Incidentally, illustrative techniques for producing cationic polymers and other water-soluble polymers include bulk polymerization, suspension polymerization, emulsion polymerization, slurry polymerization, and aqueous polymerization. Among them, the aqueous polymerization technique is in wide use, because it requires no step for removing a solvent and does not invite a toxic solvent or emulsifier to be contaminated in product polymers.

According to the aqueous polymerization technique, water-soluble polymers can be obtained as hydrous polymers having viscosity by adding a radical initiator to an aqueous solution of a radical-polymerizable monomer, and where necessary heating to an adequate temperature to perform a polymerization reaction. If necessary, the hydrous polymers are pulverized after vacuum drying or hot-air drying, or are subjected to spray drying or freeze-drying to yield powdered polymers.

The water-soluble polymers obtained by such a technique contain residual low molecular weight polymer and unreacted monomers and cannot be used as intact as drugs with safety. Therefore, the water-soluble polymers must be purified in a purification step. Such purification techniques for polymers include fractionation, reprecipitation, and ultrafiltration, as well as adsorptive removal, and filtration with a permselective membrane as special techniques. Each of these techniques is, however, complicated and time-consuming.

The present inventors attempted to purify the cationic polymer (III) by ultrafiltration, but this purification was disadvantageous in that it required a long time to perform an ultrafiltration step and a drying step to thereby increase required energy and costs. In addition, during these steps, the cationic polymer (III) was hydrolyzed to form a hydrolysis product or quaternarizing agent moiety ($R^3X$) was eliminated from the quaternary ammonium salt moiety. When the time required for drying was prolonged, an undesirable necessary crosslinking reaction occurred to make it difficult to redissolve the dried polymer, and the polymer could not be significantly prepared into a drug in some cases. When polymers were obtained by ultrafiltration under the same condition and were tabletted, the resulting tablets might show variations in disintegratability.

The present invention has been accomplished under these circumstances. Accordingly, it is an object of the invention to provide a process for producing a cationic polymer capable of ensuring the safety as a drug and capable of producing and purifying the object polymer with high efficiency, in the production of a specific cationic polymer having a marked cholesterol-lowering activity.

SUMMARY OF THE INVENTION

The invention provides a process for producing a cationic polymer having a cholesterol-lowering activity to reduce the amount of a low molecular weight polymer having a weight average molecular weight of 10,000 or less, an unreacted monomer, and a degradation product, and the process including the steps of:

(1) subjecting a water-soluble monomer component essentially containing a cationic monomer represented by the following formula (I) to aqueous polymerization in such a manner that the viscosity of a polymerization reaction solution is equal to or more than 1,000 cps and less than 300,000 cps at the point of time when a polymerization rate reaches 90%;

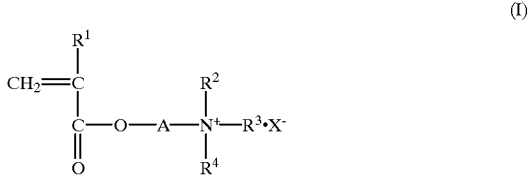

(wherein $R^1$ is H or a methyl group; $R^2$, $R^3$, and $R^4$ are each independently H, an alkyl group, or an aralkyl group; A is an alkylene group; $X^-$ is a counter anion)

(2) continuing the polymerization until the polymerization rate exceeds 95%;

(3) subjecting the obtained aqueous polymer to ultrafiltration;

(4) subjecting the obtained ultrafiltrated residue to concentration under depressurization at a temperature of the solution lower than 100° C.; and (5) drying a product after the depressurized concentration at a temperature $D_1$ (° C.) for a time $T_1$ (second), both parameters satisfying the following mathematical relational expression, until the water content of a resulting cationic polymer reaches 10% by weight or less:

$$350 \geq D_1 \times Log_{10} T_1$$

where $100 \leq D_1 \leq 180$ $T_1 > 1$

When the drying step is performed at a temperature lower than 100° C., the product is dried at a temperature $D_2$ (° C.) for a time $T_2$ (min.) both satisfying the following mathematical relational expressions, until the water content of a resulting cationic polymer reaches 10% by weight or less:

$$300 \geq D_2 \times Log_{10} T_2$$

where $10 \leq D_2 < 100$ $T_2 > 1$

DETAILED DESCRIPTION OF THE PREFFERRED EMBODYMENTS OF THE INVENTION

The present inventors made investigations to pursue the causes of the above problems, and found, for example, that a specific polymerization technique can reduce unreacted monomers and low molecular weight polymer which adversely affect the safety, that harmful effects such as deteriorated efficiencies of the ultrafiltration step and drying step are caused by an ultra high molecular weight polymer in the polymerization product, that these unreacted monomers and low molecular weight polymer can be further reduced and removed by ultrafiltration, and that if the condition in the drying step is not selected appropriately, a quaternarizing agent which may have safety problem is eliminated from the polymer, which is liable to contaminate the product cationic polymer above the allowable amount.

Specifically, the inventors found that when a polymerization reaction solution has a viscosity of 300,000 cps or more, the end product polymer, as a result, contains large amount of ultra high molecular weight cationic polymers, which causes the following disadvantages.

(1) An ultrafiltration rate becomes extremely low to invite the ultrafiltration step to require a long time. In contrast, if the viscosity of a solution to be filtreated is reduced to yield a dilute solution in order to increase the filtration rate, concentration and drying of a residual solution require enormous amount of energy and increased costs.

(2) Ester groups in the cationic polymer are liable to be hydrolyzed, and if a dilute solution is subjected to ultrafiltration, the ester groups become more liable to be hydrolyzed in the ultrafiltration step. The drug efficacy is therefore adversely affected.

(3) The time-consuming drying step increases impurities due to the hydrolysis of the cationic polymer or causes the elimination of the quaternarizing agent.

(4) If the cationic polymer contains large amount of ultra high molecular weight polymers, redissolution after drying and powdering the polymer requires a long time, and the resulting solution may be heterogeneous because a part of the powdered polymer is liable to aggregate in the redissolution, thereby deteriorating the disintegration property in the form of a tablet or another solid preparation.

The inventors also found that if the product is dried at high temperature in the last drying step to improve the drying efficiency, the quaternarizing agent is eliminated from the quaternary ammonium salt moiety of the cationic polymer to be an impurity, and that the impurity increases due to long-time drying even at low temperature.

Accordingly, the invention provides a process for producing a cationic polymer which contains reduced amount of the impurities such as low molecular weight polymer, unreacted monomer, hydrolysis product, quaternarizing agent, and the like, and concurrently includes reduced amount of ultra high molecular weight polymer, by polymerizing a monomer component essentially containing a cationic monomer (I) under the specific condition and ultrafiltrating and drying the obtained polymer under the specific condition.

The use of the invented process can efficiently yield a cationic polymer having a cholesterol-lowering activity while ensuring the safety as a drug. The invention will be illustrated in further detail below. The term "polymer" as used in the invention means and includes not only homopolymer but also copolymer and other multi-polymer.

To obtain a cationic polymer having a cholesterol-lowering activity obtain according to the invention, a monomer component containing a cationic monomer (I) represented by the following formula as an essential monomer (in a proportion of preferably 20% by mole or more, and more preferably 100% by mole in the overall monomers) is polymerized:

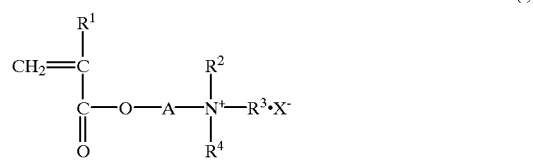

(I)

(wherein $R^1$ is H or a methyl group; $R^2$, $R^3$, and $R^4$ are each independently H, an alkyl group, or an aralkyl group; A is an alkylene group; and $X^-$ is a counter anion).

The monomer (I) will now be described in more detail. In the substituents $R^2$, $R^3$, and $R^4$, the alkyl group includes, but is not limited to, straight- or branched chain alkyl groups each having 1 to 20 carbon atoms including from methyl, ethyl, propyl, butyl, and other lower alkyl groups to icosyl group. The aralkyl group includes benzyl group and the like. The group A is, for example, methylene group, ethylene group, propylene group, and butylene group. $X^-$ is a physiologically acceptable contour ion. Such physiologically acceptable counter ions include, but are not limited to, anions of a carbonate, a bicarbonate, a formate, an acetate, a sulfate, a propionate, a malonate, a succinate, a fumarate, an ascorbate, a phosphate, a sulfonate, a halide, or a glucuronate, as well as anions of amino acids such as glutamic acidandaspartic acid. Among them, $Cl^-$, $Br^-$, $I^-$, and other halide ions, and phosphate and sulfonate ions are desirable.

Concrete examples of the cationic monomer (I) include quaternarized monomers obtained by subjecting a monomer to react with a known quaternarizing agent, and their salts with, for example, hydrochloric acid, sulfuric acid, or nitric acid. Such material monomers include, for example, dimethylaminoethyl (meth)acrylate, diethylaminoethyl (meth)acrylate, dimethyl aminopropyl (meth)acrylate, 2-hydroxydimethyl aminopropyl (meth)acrylate, and aminoethyl acrylate. The quaternarizing agent includes, but is not limited to, methyl chloride, methyl bromide, ethyl chloride, ethyl bromide, benzyl chloride, benzyl bromide, dimethyl sulfate, and diethyl sulfate.

The other monomers copolymerizable with the monomer (I) include, but are not limited to, dimethylaminoethyl (meth)acrylate, diethylaminoethyl (meth)acrylate, dimethyl aminopropyl (meth)acrylate, diethylaminopropyl (meth)acrylate, 2-hydroxydimethylaminopropyl (meth)acrylate, aminoethyl (meth)acrylate, and other amino-group-containing monomers, or their salts with, for example, hydrochloric acid, bromic acid, sulfuric acid, nitric acid, acetic acid, or propionic acid;

- (meth)acrylic acid, maleic acid, fumaric acid, itaconic acid, crotonic acid, and other carboxyl-group-containing monomers or their salts with, for example, monovalent metals, divalent metals, ammonia, or organic amine compounds;
- (meth)acrylamide, t-butyl(meth)acrylamide, and other amido-group-containing monomers;
- vinylsulfonic acid, allylsulfonic acid, methallylsulfonic acid, 2-acrylamido-2-methylpropanesulfonic acid, 3-allyloxy-2-hydroxysulfonic acid, sulfoethyl (meth)acrylate, sulfopropyl (meth)acrylate, 2-hydroxysulfopropyl (meth)acrylate, sulfoethylmaleimide, and other sulfonic-acid-group-containing monomers, or their salts with, for example, monovalent metals, divalent metals, ammonia, or organic amine compounds;
- hydroxyethyl (meth)acrylate, polyethylene glycol mono (meth)acrylate, polyethylene glycol monoisoprenol ether, polyethylene glycol monoallyl ether, hydroxypropyl (meth)acrylate, polypropylene glycol mono (meth)acrylate, polypropylene glycol monoisoprenol ether, polypropylene glycol monoallyl ether, α-hydroxyacrylic acid, N-methylol (meth)acrylamide, vinyl alcohol, allyl alcohol, 3-methyl-3-buten-1-ol (isoprenol), glycerol monoallyl ether, and other hydroxyl-group-containing monomers;
- methyl (meth)acrylate, ethyl (meth)acrylate, and other (meth)acrylates;
- styrene, α-methylstyrene, vinyl acetate, vinylpyrrolidone, and vinyl ethers, and the like.

Each of these monomers, alone or in combination, can be used concurrently with the essential monomer (I) within the range not deteriorating the solubility in water and safety of the resulting polymer. The proportion of these monomers should be preferably less than 80% by mole in the overall monomer component. This range is defined because the resulting polymer may not exhibit a satisfactory cholesterol-lowering activity, and the amount of these monomers should be preferably minimized from this viewpoint The monomer component essentially comprising the monomer (I) is polymerized by aqueous polymerization. The aqueous polymerization is performed by adding a water-soluble radical polymerization initiator to an aqueous solution of the monomer component, and where necessary heating the mixture as appropriate. In the aqueous polymerization, the proportion of the monomer component (monomer concentration) relative to the total of a reaction solution in a polymerization reactor is usually 2% to 60% by weight. An excessively low monomer concentration invites energy loss in the ultrafiltration step and subsequent steps. In contrast, if the monomer concentration is excessively high, a polymerization temperature cannot be significantly controlled, and an aqueous solution of the produced polymer is difficult to be handled due to its increased viscosity. The monomer concentration is preferably 4% by weight or more, or more preferably 20% by weight or more. The monomer concentration is preferably 55% by weight or less, or more preferably 45% by weight or less. The concentration may be adjusted by adding water as a solvent to the polymerization reactor after the initiation of polymerization.

Water-soluble radical polymerization initiators for use in the polymerization include, but are not limited to, peroxides such as hydrogen peroxide, peracetic acid, and the like, and peroxodisulfates such as ammonium peroxodisulfate, sodium peroxodisulfate, potassium peroxodisulfate, and the like. Sodium hydrogensulfite, L-ascorbic acid, or another reducing agent can be used concurrently with any of these peroxides and peroxodisulfates. Azobis-base initiators such as 2,2'-azobis(2-amidinopropane) hydrochloride can be also employed. Each of these initiators can be used alone or in combination. Methanol, acetone, and other water-soluble organic solvents can be added to the aqueous solution of the monomer in the polymerization within the range not deteriorating the advantages of the invention.

The invented process essentially comprises, in the aqueous polymerization, (1) a step for subjecting a water-soluble monomer component essentially comprising a cationic monomer represented by the formula (I) to aqueous polymerization in such a manner that the viscosity of a polymerization reaction solution is equal to or more than 1,000 cps and less than 300,000 cps at the point of time when the polymerization rate reaches 90%, and (2) a step for continuing the polymerization until the polymerization rate exceeds 95%.

According to the invented process, the viscosity of the polymerization reaction solution must be less than 300,000 cps at the point of time when the polymerization rate reaches 90%. The viscosity of the polymerization reaction solution is a viscosity as determined by sampling a polymerization reaction solution from the polymerization reactor during the aqueous polymerization, cooling the sampled solution to 40° C., and measuring the viscosity of the cooled solution with a Brookfield viscometer. When the viscosity of the polymerization reaction solution is 300,000 cps or more, it indicates excessively large amount of ultra high molecular weight polymers, and the aforementioned detrimental effects due to ultra high molecular weight polymers cannot be prevented. The viscosity of the polymerization reaction solution should, however, be preferably 1,000 cps or more. The viscosity of the polymerization reaction solution less than 1,000 cps indicates low molecular weight polymer exists in large amount. This is not preferable in the aspect of the polymerization efficiency. And the resulting polymer may not significantly exhibit the cholesterol-lowering activity. The more preferred lower limit of the viscosity is 5,000 cps. The concentration of a polymer in the polymerization reaction solution also affects the viscosity of the polymerization reaction solution, and the polymer concentration depends on the aforementioned monomer concentration in the aqueous polymerization. According to the invented process, therefore, the viscosity of the reaction solution at the point of time when the polymerization rate reaches 90% is specified in the above range in the case that the aqueous polymerization is performed at a monomer concentration of 2% to 60% by weight.

In the invented process, it is necessary to obtain the polymerization rate at 95% or more at the termination of the step (2). It is more preferable to obtain the polymerization rate of 98% or more. If the polymerization rate is less than 95%, that is, unreacted monomers reside in a proportion of 5% by weight or more, the ultrafiltration treatment in the step (3) requires an excessively long time. Such unreacted monomers are residual monomers which have been added to the polymerization reactor and have not been converted into polymer. The content of unreacted monomers should be preferably less than 0.05% by weight in a dried polymer obtained as an end product. This is because the safety as a drug cannot be ensured if the content of unreacted monomers is 0.05% by weight or more. In this invention, the polymerization rate is determined by sequentially sampling a reaction solution in the polymerization reactor, analyzing the amount of unreacted monomers with liquid chromatography, and calculating the conversion rate (% by weight) from added monomers (weights) to polymers (weights).

After the polymerization, a step for ultrafiltration (third step) of the obtained cationic polymer is performed. The ultrafiltration step in the invented process is to filtrate and remove the impurities such as low molecular weight polymer, unreacted monomers, and the like, from an aqueous solution of the polymer with the use of a membrane (ultrafiltration membrane) having pores 1 to 1000 nm in diameter. The aqueous solution may be appropriately diluted where necessary. "UF-PS" Series manufactured by Tosoh Corporation, "Prostack UF", "UFC4LTK", "Biomax", and "Pellicon 2" each manufactured by Nippon Millipore Co., Ltd., and the like, can be used as the ultrafiltration membrane. The pore size (molecular weight of the matter to be separated) can be freely selected according to the amount of low molecular weight polymer and impurities to be removed, but the upper limit of the pore size is preferably 500 nm, and more preferably 200 nm. Low molecular weight polymer in the ultimately obtained polymer should be preferably reduced to 10% by weight or less by ultrafiltration. The low molecular weight polymer at this level will not adversely affect the safety. The content of the low molecular weight polymer should be more preferably 6% by weight or less.

Then in a step (fourth step), the ultrafiltrated residual solution is subjected to for depressurized concentration at a temperature of the solution lower than 100° C., and in a drying step (fifth step), the concentrated solution is dried under specific condition to yield a dried product of the cationic polymer.

As to condition for the depressurized concentration, the degree of pressure reduction is not particularly limited as far as the temperature of the solution is set to be lower than 100° C. A film evaporator, and a rotary evaporator can be used for concentrating under reduced pressure, for example. From the viewpoint of the efficiency of depressurized concentration, the temperature of the solution should be preferably 10° C. or higher, and more preferably 20° C. or higher. The depressurized concentration at temperature exceeding 100° C., however, causes hydrolysis of the ester groups to deteriorate the polymer. In addition, a hydrolysis product shown by the following formula (II) is formed.

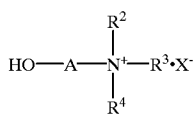

(II)

(wherein A, $R^2$, $R^3$, $R^4$, and $X^-$ are the same with A, $R^2$, $R^3$, $R^4$, and $X^-$ in the compound represented by the formula (I).)

The content of the hydrolysis product in the ultimately obtained cationic polymer should be preferably 0.05% by weight or less. If the content is more than 0.05% by weight, the safety as a drug is deteriorated. The temperature in this step is -more preferably 80° C. or lower. The depressurized concentration step shortens a drying time in the subsequent drying step.

In the drying step, a specific drying condition should be selected. This is because the aforementioned quaternarizing agent (e.g., methyl chloride and benzyl chloride) for use in the formation of the cationic monomer represented by the formula (I) is found to be eliminated from the quaternary ammonium salt moiety of the polymer. The quaternarizing agent is represented by $R^3X$, where $R^3$ and $X$ are the same with $R^3$ and $X$ in the compound represented by the formula (I). The content of the quaternarizing agent in the cationic polymer may be preferably reduced to 0.05% by weight or less in consideration of the safety as a drug.

To this end, the present inventors made investigations, and found that it is required to select a drying condition that satisfied the following mathematical relational expression (1) in the drying at temperature ranging from 100° C. to 180° C., where a drying temperature is $D_1$ (° C.) and a drying time is $T_1$ (sec.)

$$350 \geq D_1 \times \mathrm{Log}_{10} T_1 \tag{1}$$

where
$100 \leq D_1 \leq 180$
$T_1 > 1$

When the drying is performed at temperature of 100° C. or higher, the quaternarizing agent is extremely liable to be eliminated from the cationic polymer, and the time $T_1$ (sec.) must be shortened so as to satisfy the above condition. If the polymer is dried under such a condition that the value in the left hand side of the above mathematical expression exceeds 350, the quaternarizing agent in the cationic polymer exceeds the target limit, 0.05% by weight. The value in the left hand side of the mathematical expression is preferably 320 or less, and more preferably 290 or less. Separately, the upper limit of the drying temperature $D_1$ is set to 180° C., as the cationic polymer is markedly deteriorated if $D_1$ exceeds 180° C. The more preferable upper limit of the drying temperature $D_1$ is 160° C.

When the water content of the cationic polymer becomes 10% by weight or less, the drying step is brought to an end. The time $T_1$ should be more then 1 second. If $T_1$ is less than 1 second, the drying time is too short to render the water content 10% by weight or less.

If the cationic polymer is dried at temperature lower than 100° C., it is to be dried under normal pressure or reduced pressure The drying should be preferably performed under reduced pressure to improve the drying efficiency. The drying condition is selected so as to satisfy the following mathematical relational expression (2), where a drying temperature is $D_2$ (° C.), and a drying time is $T_2$ (min.)

$$300 \geq D_2 \times \mathrm{Log}_{10} T_2 \tag{2}$$

where $10 \leq D_2 > 100$ $T_2 > 1$

At temperature lower than 100° C., the quaternarizing agent may not be relatively eliminated from the cationic polymer, and $T_2$ can be significantly elongated as compared with cases where the drying temperature is 100° C. or higher. If the polymer is dried under such a condition where the value in the left hand side of the above mathematical expression exceeds 300, the content of the quaternarizing agent in the resulting cationic polymer exceeds 0.05% by weight. In contrast, if the drying temperature is excessively low, the drying step requires an excessively long time, and the lower limit of $D_2$ is set to 10° C., and more preferably 20° C., from the viewpoint of drying efficiency. The value in the left hand side of the above mathematical expression may be preferably 280 or less, and more preferably 260 or less. In this case, as the drying condition is mild, the drying should be preferably performed for 1 hour or more. In this case, too, the drying step is brought to an end when the water content reaches 10% by weight or less. The water content cannot be reduced to 10% by weight or less unless $T_2$ is more than 1 minute.

If a plurality of drying steps are performed, in which drying temperatures are different and all the drying temperatures are 100° C. or higher, the expression (1) is employed where the total drying time is set to $T_1$ and the highest drying temperature is set to $D_1$. When all the drying temperatures are lower than 100° C., the expression (2) is to be employed where the total drying time is set to $T_2$ and the highest drying temperature is set to $D_2$. If plural drying temperatures include both a drying temperature lower than 100° C. and a drying temperature of 100° C. or higher, i.e., for example, when the polymer is dried at first at 80° C. for 4 hours and then at 110° C for 120 seconds, the expression (1) is to be employed where 110° C. is set to $D_1$ and 120 seconds is set to $T_1$. This is because the elimination reaction of the quaternarizing agent is liable to occur at high temperature.

The cationic polymer obtained by a series of steps according to the invented production process as described above is a polymer having a satisfactory safety and containing reduced amount of low molecular weight polymer, unreacted.monomers, hydrolysis products, quaternarizing agents, and other impurities. As the contents of these impurities in the dried cationic polymer that can ensure the safety, the contents of low molecular weight polymer having a weight average molecular weight of 10,000 or less should be 10% by weight or less, the unreacted monomer (I), the hydrolysis product, i.e., the alcohol represented by the formula (II), and the quaternarizing agent are 0.05% by weight or less, respectively. The quantity of these impurities can be determined with known analyzers. For example, the quantitative analysis of the low molecular weight polymer can be performed on a gel permeation chromatography, and unreacted monomer, hydrolysis product and quaternarizing agent can be quantitatively analyzed with a liquid chromatography.

The cationic polymer according to the invention is useful as a cholesterol-lowering drug and is made into a pharmaceutical preparation in a known manner when used in therapeutics. In the formulation, appropriate pharmaceutically acceptable additives can be used. Dosage forms of the preparation include, but are not limited to, known dosage forms such as tablets, granules, dusts, capsules, syrups, suspensions, emulsions, and solutions.

For example, a solid preparations in the form of tablets or granules can be obtained by appropriately blending with excipients, for examples sugars such as lactose, glucose, sucrose, mannitol and sorbitol, starches such as corn starch, potato starch and dextrin, microcrystalline cellulose, gum arabic, pullulan, aluminum silicate, light silicic anhydride, magnesium metasilicate aluminate, magnesium silicate, calcium phosphate, calcium carbonate and calcium sulfate, disintegrating agents such as sodium carboxymethylcellulose, carboxymethylcellulose, calcium carboxymethylcellulose, hydroxypropylcellulose, crystalline cellulose, ethyl cellulose, sodium carboxymethylstarch and sodium crosscarboxymethylcellulose, binders such as polyvinyl alcohol, polyvinyl pyrrolidone and hydroxypropyl cellulose, lubricating agents such as talc, magnesium stearate, stearic acid and calcium stearate. As additional additives, polyethylene glycols, propylene glycols and coloring agents can be blended as appropriate. As coating agents for tablets, cellulose such as hydroxypropylcellulose, hydroxypropylmethyl cellulose, methylcellulose, and the like; diethylamino methacrylate, polyvinyl acetal diethylaminoacetate, diethylaminomethacrylate-methylacrylate copolymers, and cellulose acetate N,N-di-N-butylhydroxypropyl ether.

To formulate preparations for use in the capsuled form, there may be appropriately blended together base materials for a hard or soft capsule which are geratine, sorbitol, glycerol, propylene glycol, sucrose, a plasticizer such as gum arabic, a pigments and a coloring agents such as titanium oxide, a preservatives such as methyl, ethyl or propyl p-hydroxybenzoate, perfume and other excipients.

To formulate preparations in the form syrups, suspensions, emulsions and solutions, there may be blended together solubilizers such as water, ethanol, glycerol, sorbitol, polyethylene glycol or propylene glycol, nonionic surfactants such as glycerol monostearate, polyoxyl stearate, lauromacrogol, polysorbate 80, sorbitan oleate and sucrose fatty acid esters, anionic surfactants such as stearyltriethanolamine and sodium lauryl sulfate, cationic surfactants such as benzalkonium chloride and benzethonium chloride, ampholytic surfactants such as lecithin. In addition to the above surfactants, there may be blended together suspending agents or dispersing agents, such as polyvinyl compounds such as polyvinyl alcohol and polyvinyl pyrrolidone, cellulose derivatives such as carboxymethyl cellulose sodium, methylcellulose, hydroxymethylcellulose, hydroxydiethylcellulose, hydroxypropylcellulose and hydroxypropyl methylcellulose, other materials such as gum arabic and gelatin, thickening agents such as aluminum magnesium silicate, colloidal hydrous aluminum magnesium silicate, kaolin, bentonite and microcrystalline cellulose, preservatives such as p-hydroxybenzoates, benzalkonium chloride and benzethonium chloride, flavors and sweeteners such as fructose, cocoa, invert sugars, citric acid, ascorbic acid and fruit juices, and other additives as appropriate.

Each preparations thus obtained is formulated as a cholesterol-lowering drug into a unit dose form containing from 0.01 to 3.0 g of the cationic polymer obtained by the present invention. This preparations of the cholesterol-lowering drug can be administered to a patient in a dose of from 0.1 to 9 g/day, preferably from 0.1 to 5 g/day, once to thrice a day. The cholesterol-lowering drug is preferably administered for at least such a period of time sufficient for causing a decrease in the serum cholesterol level.

EXAMPLES

The present invention will be further illustrated in detail with reference to several examples below, which are not intended to limiting the scope of the invention. Testing methods of properties employed in the examples are as follows.

(1) Viscosity of the polymerization reaction solution (cps): A polymerization reaction solution was sampled from the polymerization reactor, was adjusted to 40° C. and was subjected to measurement with a Brookfield rotary viscometer.

(2) Polymerization rate (% by weight): A polymerization reaction solution was sampled from the polymerization reactor and the amount of unreacted monomer in the sampled solution was analyzed according to a method described in (4) below, and the polymerization rate (% by weight) was determined by subtracting the obtained weight percentage of the unreacted monomer from 100% by weight.

(3) Content of low molecular weight polymer (% by weight): The cationic polymer was dissolved in a 5% by weight sodium hydroxide aqueous solution to make a 5% by weight cationic polymer solution. The resulting solution was heated at 80° C. for 8 hours to perform hydrolysis reaction of the cationic polymer. The resulting mixture was passed through a dialysis membrane (a product of Spectrum Medical Industries Co., Ltd.; "Spectra/Por Membrane MWCO1000") to eliminate sodium hydroxide to thereby yield an aqueous solution of the polymer as a filtrate. The molecular weight distribution of the hydrolyzed polymer was determined with a gel permeation chromatography (GPC) under the following analysis condition. A reference sample of sodium polyacrylate was used as a standard of molecular weights.

The molecular weight and molecular weight distribution of a polymer having a chemical structure before hydrolysis were calculated on the basis of the measurements of the hydrolyzed polymer, and percentage (% by weight) of low molecular weight polymer having a weight average molecular weight of 10,000 or less in the whole polymer was determined. In the examples, acryloyloxyethyl-N,N-dimethyl-N-benzylammonium chloride was used as the cationic monomer, the molecular weight before hydrolysis was obtained by multiplying the weight average molecular weight of the hydrolysed polymer by 2.87.

GPC Measuring Condition

Column: "asahipak GF-7MHQ" (manufactured by Showa Denko K.K.)

Detector: UV (215 nm)

Eluting solution: a solution mixture of disodium hydrogenphosphate dodecahydrate (34.5 g), sodium dihydrogenphosphate dihydrate (46.2 g), and water (4919.3 g)

(4) Quantitative analyses of unreacted monomers and hydrolysis products: The polymer was dissolved in a 0.005 mole/liter hydrochloric acid aqueous solution to a concentration of 2.5% by weight, and a 10% by weight sodium chloride aqueous solution in an amount 1.5 time as much as the dissolved polymer was added to the solution to salting out polymers. The solution mixture were filtrated at normal pressures with a No. 2 filter paper to separate precipitated polymers. Unreacted monomers and hydrolysis products in the filtrate were then quantitatively analyzed with liquid chromatography (LC) under the following condition.

LC Measuring Condition

Column: "TSK gel ODS-80Ts" (manufactured by Tosoh Corp.)

Detector: UV (215 nm)

Eluting solution: a solution mixture of an aqueous solution containing each 0.01 mole of sodium 1-octanesulfonate and perchloric acid ($HClO_4$) with acetonitrile and methanol (aqueous solution:acetonitrile:methanol=23:5:2 by weight)

(5) Quantitative analysis of eliminated quaternarizing agent: The polymer was dissolved in methanol to a concentration of 1.0% by weight and the resulting polymer solution was subjected to centrifugal filtration with an ultrafiltration membrane ("UFC4LTK" manufactured by Nippon Millipore Co., Ltd.). An eliminated quaternarizing agent in the obtained filtrate was quantitatively analyzed with liquid chromatography (LC) under the following condition.

Column: "TSK gel ODS-80Tm" (manufactured by Tosoh Corp.)

Detector: UV (215 nm)

Eluting solution: a solution mixture of water and acetonitrile (3:2 by weight)

(6) Water content of dried polymer: A powdered polymer was dissolved in a solvent mixture to a concentration of 2.0% by weight, and the water(moisture) content of the resulting solution was measured with a Karl Fischer's moisture meter. The above solvent mixture contained 5 ml of acetonitrile and 20 ml of a dehydrated solvent ("Dehydrated Solvent SU" manufactured by Mitsubishi Chemical Corp.).

(7) Viscosity of 1% aqueous solution of polymer after drying step (cps): A resulting polymer after the drying step was dissolved in water to a concentration of 1% by weight, and the viscosity of the resulting solution was measured with a Brookfield rotary viscometer at 25° C.

Example 1

Into a 2.5-L kneader with a thermometer, a nitrogen inlet tube, and a reflux condenser, 400 g of acryloyloxyethyl-N, N-dimethyl-N-benzylammonium chloride and 600 g of water were charged, and the inner atmosphere was replaced with nitrogen and the inner temperature was adjusted to 50° C. 14.0 g of 20% by weight 2,2'-azobis(2-amidinopropane) dihydrochloride aqueous solution was then added as a polymerization initiator to the mixture while stirring at 30 rpm under normal pressure. Sixteen minutes after the addition of the polymerization initiator, the polymerization rate reached 90%, and the viscosity of a polymerization reaction solution in the reactor was 42,000 cps at this point. The reaction temperature attained the maximum (75° C.) 23 minutes after the addition of the polymerization initiator. The polymerization rate reached 99% 60 minutes after the reaction temperature attained maximum, and then the polymerization was terminated. At this stage, the amount of a low molecular weight polymer, an unreacted monomer, a hydrolysis product hydroxyethyl-N,N-dimethyl-N-benzylammonium chloride (hereinafter briefly referred to as "HEBC"), and an eliminated quaternarizing agent benzyl chloride in the polymerization reaction solution were respectively 12.2% by weight, 0.90% by weight, 0.09% by weight, and less than 0.01% by weight (level below the capability of a measuring apparatus) relative to solid contents of the polymer in the polymerization reaction solution.

200 g of the polymerization reaction solution was diluted 10 times and the diluted solution was subjected to an ultrafiltration treatment with an ultrafiltration membrane ("Prostack UF": molecular weight of the matter to be separated is 100,000: manufactured by Nippon Millipore Co., Ltd.). The ultrafiltration treatment was performed for 4 hours while adding the same amount of water with that of the filtrate to the solution to be treated, in order to prevent the viscosity of the solution from increasing due to the concentration of the solution during the ultrafiltration treatment. The amount of a low molecular weight polymer, an unreacted monomer, HEBC, and benzyl chloride in the obtained residual solution (not a filtrate but a aqueous polymer solution remained over the ultrafiltration membrane) were respectively 5.5% by weight, 0.01% by weight, 0.025% by weight, and less than 0.01% by weight (level below the capability of a measuring apparatus) relative to the solid contents of the polymer. The results show that the low molecular weight polymer, unreacted monomer, and HEBC were significantly removed by the ultrafiltration.

The residual solution (aqueous polymer solution) after the ultrafiltration was concentrated with a rotary evaporator at 60° C. at a reduced pressure of 30 mmHg and a concentrated solution containing 25.8% by weight of solid contents was obtained.

The concentrated solution was then dried with a vacuum drier at 60° C. (corresponding to $D_2$) at a reduced pressure of 50 mmHg for 24 hours (1440 minutes: corresponding to $T_2$). In this case, $D_2 \times \text{Log}_{10} T_2$ was 189.5. The water content of the polymer after drying was 8.9% by weight.

The dried product was further pulverized and classified, and a powdered polymer having a particle size of 200 to 50 mesh was obtained. The contents of a low molecular weight polymer, unreacted monomer, HEBC, and benzyl chloride in the powdered polymer were respectively 5.3% by weight, 0.01% by weight, 0.027% by weight, and 0.01% by weight. The results show that a hydrolysis reaction and an elimination reaction of the quaternarizing agent did not significantly occur during the concentration and drying steps. The powdered polymer had a viscosity as a 1% aqueous solution of 70 cps.

Example 2

A powdered polymer was obtained by performing a polymerization, ultrafiltration, concentration, and drying steps in the same manner as in Example 1, except that the concentrated solution was dried with a double drum drier at 110° C. (corresponding to $D_1$) under atmospheric pressure for 120 seconds (corresponding to $T_1$). In this example, $D_1 \times \text{Log}_{10} T_1$ was 228.7. The water content of the dried polymer was 6.4% by weight.

The contents of a low molecular weight polymer, unreacted monomer, HEBC, and benzyl chloride in the powdered polymer were respectively 5.6% by weight, 0.01% by weight, 0.03% by weight, and 0.01% by weight relative to the polymer. The polymer had a viscosity as a 1% aqueous solution of 68 cps.

Example 3

A powdered polymer was obtained by performing a polymerization, ultrafiltration, concentration, and drying steps in the same manner as in Example 1, except that the concentrated solution was dried with a double drum drier at 110° C. (corresponding to $D_1$) under atmospheric pressure for 360 seconds (corresponding to $T_1$). In this example, $D_1 \times \text{Log}_{10} T_1$ was 281.2. The water content of the dried polymer was 5.9% by weight.

The contents of a low molecular weight polymer, unreacted monomer, HEBC, and benzyl chloride in the powdered polymer were respectively 5.0% by weight, 0.01% by weight, 0.02% by weight, and 0.04% by weight relative to the polymer. The polymer had a viscosity as a 1% aqueous solution of 67 cps.

Example 4

A powdered polymer was obtained by performing a polymerization, ultrafiltration, concentration, and drying steps in the same manner as in Example 1, except that the concentrated solution was dried with a double drum drier at 130° C. (corresponding to $D_1$) under atmospheric pressure for 30 seconds (corresponding to $T_1$). In this example, $D_1 \times \text{Log}_{10} T_1$ was 192.0. The water content of the dried polymer was 3.4% by weight.

The contents of a low molecular weight polymer, unreacted monomer, HEBC, and benzyl chloride in the powdered polymer were respectively 5.2% by weight, 0.01% by weight, 0.02% by weight, and 0.02% by weight relative to the polymer. The polymer had a viscosity as a 1% aqueous solution of 65 cps.

Example 5

Into a 2.5-L kneader with a thermometer, a nitrogen inlet tube, and a reflux condenser, 400 g of acryloyloxyethyl-N, N-dimethyl-N-benzylammonium chloride and 596 g of water were charged, and the inner atmosphere was replaced with nitrogen and the inner temperature was adjusted to 40° C. 9 g of 4.5% by weight ammonium peroxodisulfate aqueous solution was then added as a polymerization initiator to the mixture, and 20 seconds later 9 g of 1% by weight sodium hydrogensulfite aqueous solution was added to the mixture, while stirring at 30 rpm under normal pressure. The polymerization rate reached 90% 10 minutes after the addition of the polymerization initiator, and the viscosity of the polymerization reaction solution in the reactor was 98,000 cps at this point. The reaction temperature attained the maximum (66° C.) about 12 minutes after the addition of the polymerization initiator. The polymerization rate reached 98% after 30-minute stirring from the time when the reaction temperature attained the maximum, and the polymerization was terminated. At this stage, the amount of a low molecular weight polymer, an unreacted monomer, HEBC, and benzyl chloride in the polymerization reaction solution were respectively 1.5% by weight, 1.85% by weight, 0.02% by weight, and less than 0.01% by weight relative to solid contents of the polymer in the polymerization reaction solution.

200g of the polymerization reaction solution was diluted 10 times and then the diluted solution was subjected to an ultrafiltration treatment in the same manner as in Example 1. The amount of the low molecular weight polymer, unreacted monomer, HEBC, and benzyl chloride in the obtained residual solution (aqueous polymer solution) were respectively 0.9% by weight, 0.02% by weight, 0.01% by weight, and less than 0.01% by weight relative to the solid contents of the polymer.

The residual solution (aqueous polymer solution) after the ultrafiltration was concentrated with a rotary evaporator at 80° C. at a reduced pressure of 50 mmHg and a concentrated solution containing 19.0% by weight of solid contents was obtained.

The concentrated solution was then dried with a vacuum drier at 80° C. (corresponding to $D_2$) at a reduced pressure of 30 mmHg for 25 hours (1,500 minutes: corresponding to $T_2$). In this case, $D_2 \times \text{Log}_{10} T_2$ was 254.1. The water content of the dried polymer was 5.3% by weight.

The dried product was further pulverized and classified, and a powdered polymer having a particle size of 200 to 50 mesh was obtained. The contents of a low molecular weight polymer, unreacted monomer, HEBC, and benzyl chloride in the powdered polymer were respectively 1.0% by weight, 0.01% by weight, 0.02% by weight, and 0.01% by weight relative to the polymer. The powdered polymer had a viscosity as a 1% aqueous solution of 95 cps and a weight average molecular weight of about 2,700,000.

Comparative Example 1

A powdered polymer was obtained by performing polymerization and drying steps in the same manner as in Example 1, except that ultrafiltration and depressurized concentration steps were not conducted. The polymer after drying had a water content of 8.6% by weight. The contents of a low molecular weight polymer, unreacted monomer, HEBC, and benzyl chloride in the powdered polymer were respectively 12.4% by weight, 0.81% by weight, 0.11% by weight, and 0.01% by weight relative to the polymer. The polymer had a viscosity as a 1% aqueous solution of 62 cps.

Comparative Example 2

A powdered polymer was obtained by performing polymerization, ultrafiltration, concentration, and drying steps in the same manner as in Example 1, except that the concentrated solution was dried with a hot-air drier at 110° C. (corresponding to $D_1$) under atmospheric pressure for 86,400 seconds (corresponding to $T_1$). In this example, $D_1 \times \text{Log}_{10} T_1$ was 543.0. The water content of the dried polymer was 5.4% by weight.

The contents of a low molecular weight polymer, unreacted monomer, HEBC, and benzyl chloride in the powdered polymer were respectively 5.9% by weight, 0.01% by weight, 1.35% by weight, and 0.23% by weight relative to the polymer. The polymer had a viscosity as a 1% aqueous solution of 65 cps.

Comparative Example 3

A powdered polymer was obtained by performing polymerization, ultrafiltration, concentration, and drying steps in the same manner as in Example 1, except that the concentrated solution was dried with a double drum drier at 110° C. (corresponding to $D_1$) under atmospheric pressure for 1,800 seconds (corresponding to $T_1$). In this example, $D_1 \times \text{Log}_{10} T_1$ was 358. The dried polymer had a water content of 5.5% by weight.

The contents of a low molecular weight polymer, unreacted monomer, HEBC, and benzyl chloride in the powdered polymer were respectively 6.3% by weight, 0.01% by weight, 0.03% by weight, and 0.09% by weight relative to the polymer. The polymer had a viscosity as a 1% aqueous solution of 68 cps.

Comparative Example 4

A powdered polymer was obtained by performing polymerization, ultrafiltration, concentration, and drying steps in the same manner as in Example 1, except that the concentrated solution was dried with a vacuum drier at 80° C. (corresponding to $D_2$) at a reduced pressure of 50 mmHg for 168 hours (10,080 minutes: corresponding to $T_2$). In this example, $D_2 \times \text{Log}_{10} T_2$ was 320.3. The dried polymer had a water content of 5.1% by weight.

The contents of a low molecular weight polymer, unreacted monomer, HEBC, and benzyl chloride in the powdered polymer were respectively 5.5% by weight, 0.01% by weight, 0.04% by weight, and 0.10% by weight relative to the polymer. The polymer had a viscosity as a 1% aqueous solution of 68 cps.

Comparative Example 5

A powdered polymer was obtained by performing polymerization, ultrafiltration, concentration, and drying steps in the same manner as in Example 1, except that the concentration step was performed at 102° C. to 104° C. under atmospheric pressure. The dried polymer had a water content of 9.0% by weight.

The contents of a low molecular weight polymer, unreacted monomer, HEBC, and benzyl chloride in the powdered polymer were respectively 5.5% by weight, 0.01% by weight, 0.42% by weight, and 0.01% by weight relative to the polymer. The polymer had a viscosity as a 1% aqueous solution of 66 cps. The results show that HEBC considerably increased.

Comparative Example 6

Into a polymerization reactor similar to that in Example 1, 440 g of acryloyloxyethyl-N,N-dimethyl-N-benzylammonium chloride and 636 g of water were charged, and the inner atmosphere was replaced with nitrogen and the inner temperature was adjusted to 40° C. 12 g of 0.380% by weight ammonium peroxodisulfate aqueous solution as a polymerization initiator and successively 12 g of 0.158% by weight sodium bisulfite aqueous solution were added to the mixture, while stirring at 30 rpm under normal pressure The reaction temperature attained the maximum (61° C.) 6 minutes after the addition of the polymerization initiator. The polymerization rate reached 90% ten minutes after the addition of the polymerization initiator, and the viscosity of the polymerization reaction solution in the reactor was 360,000 cps at this point. The relatively high viscosity shows that a polymer having high molecular weight were formed. The polymerization rate reached 96% after 30-minutes stirring from the time when the temperature attained the maximum, and then the polymerization was terminated. At this stage, the amount of a low molecular weight polymer, an unreacted monomer, HEBC, and benzyl chloride in the polymerization reaction solution were respectively 1.2% by weight, 4.02% by weight, 0.02% by weight, and less than 0.01% by weight relative to solid contents of the polymer in the polymerization reaction solution. 100 g of the polymerization reaction solution was diluted 20 times and the diluted solution was subjected to an ultrafiltration treatment in the same manner as in Example 1. The amount of a low molecular weight polymer, an unreacted monomer, HEBC, and benzyl chloride in the obtained residual solution (aqueous polymer solution) were respectively 0.8% by weight, 0.81% by weight, 0.02% by weight, and less than 0.01% by weight relative to the solid contents of the polymer.

The aqueous polymer solution after the ultrafiltration was concentrated with a rotary evaporator at 60° C. at a reduced pressure of 30 mmHg and a concentrated solution containing 13.2% by weight of solid contents was obtained.

The concentrated solution was then dried with a drier at 60° C. (corresponding to $D_2$) at a reduced pressure of 50 mmHg for 24 hours (1,440 minutes: corresponding to $T_2$). In this case, $D_2 \times \text{Log}_{10} T_2$ was 189.5. The water content of the polymer after drying was 9.2% by weight.

The dried product was further pulverized and classified to yield a powdered polymer having a particle size of 200 to 50 mesh. The contents of a low molecular weight polymer, an unreacted monomer, HEBC, and benzyl chloride in the powdered polymer were respectively 0.9% by weight, 0.41% by weight, 0.03% by weight, and 0.03% by weight. The polymer had a viscosity as a 1% aqueous solution of 246 cps and a weight average molecular weight of about 5,900,000. The results demonstrate that the polymer had a relatively high molecular weight.

(Disintegration Test of Tablets)

To 60 g of each of the powdered polymers obtained according to Examples 1 to 5 and Comparative Examples 1 to 6, 10 g of microcrystalline cellulose, 14 g of lactose, 15 g of carboxymethyl-cellulose calcium, and 1 g of magnesium stearate were added, and the resulting mixtures were molded at a pressure of 1 ton and a series of tablets having a diameter of 6 mm and a weight of 250 mg was obtained.

Each of the obtained tablets was inserted in 100 ml of water (37±2° C.) stirred with a magnetic stirrer, the stirring was continued for further 10 minutes, and the disintegration of the tablet was then observed. The disintegration property was evaluated according to the following criteria.

Good:

The tablet was completely disintegrated within 10 minutes and a homogeneous aqueous solution was obtained.

Poor:

Disintegration of the tablet was observed but undissolved part was partially remained after 10-minute stirring.

TABLE 1

| | Example | | | | | Comparative Example | | | | | |
|---|---|---|---|---|---|---|---|---|---|---|---|
| | 1 | 2 | 3 | 4 | 5 | 1 | 2 | 3 | 4 | 5 | 6 |
| Tablet Disintegratability | Good | Good | Good | Good | Good | Good | Good | Good | Good | Good | Poor |

Industrial Applicability

According to the invented process, cationic polymers containing reduced amount of low molecular weight polymer and unreacted monomers and having a satisfactory safety can be obtained. In addition, according to the invented process, unnecessary high molecular weight polymers can be reduced, and such problems can be solved that disintegratability as a solid pharmaceutical preparation such as a tablet is deteriorated and that an ultrafiltration step and a drying step of obtained polymers require a long time to increase required energy and costs. Furthermore, hydrolysis products, quaternarizing agents, and other impurities can be prevented from forming by finding and setting optimum condition for the ultrafiltration step and the drying step.

Accordingly, the cationic polymers obtained by the invented process can be used as safety and useful cholesterol-lowing drugs by formulating into preparations.

What is claimed is:

1. A process for producing a cationic polymer having a cholesterol-lowering activity to thereby reduce the amount of a low molecular weight polymer fraction having a weight average molecular weight of 10,000 or less, an unreacted monomer, and a degradation product, said process comprising the steps of:

(1) polymerizing a water-soluble monomer component comprising a cationic monomer represented by the following formula (I) in an aqueous solution, thereby forming a polymerization reaction solution having a viscosity equal to or more than 1,000 cps and less than 300,000 cps at the point of time when a polymerization rate reaches 90%:

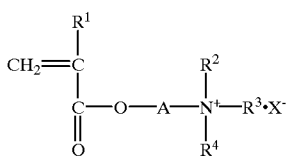

(I)

wherein $R^1$ is H or a methyl group; $R^2$, $R^3$, and $R^4$ are each independently H, an alkyl group, or an aralkyl group; A is an alkylene group; and $X^-$ is a counter anion (2) continuing the polymerization until the polymerization rate exceeds 95%;

(3) purifying the obtained aqueous polymer by ultrafiltration;

(4) concentrating the obtained ultrafiltrated residue by depressurization at a temperature of the solution lower than 100° C.; and (5) drying the obtained concentrated solution after the depressurized concentration at a temperature $D_1$ (° C.) for a time $T_1$ (second), both parameters satisfying the following mathematical relational expression, until the water content of a resulting cationic polymer reaches 10% by weight or less:

$$350 \geq D_1 \times \text{Log}_{10} T_1$$

where
   $100 \leq D_1 \leq 180$
   $T_1 > 1$.

2. A process for producing a cationic polymer having a cholesterol-lowering activity to thereby reduce the amount of a low molecular weight polymer fraction having a weight average molecular weight of 10,000 or less, an unreacted monomer, and a degradation product, said process comprising the steps of:

(1) polymerizing a water-soluble monomer component comprising a cationic monomer represented by the following formula (I) in an aqueous solution, thereby forming a polymerization reaction solution having a viscosity equal to or more than 1,000 cps and less than 300,000 cps at the point of time when a polymerization rate reaches 90%:

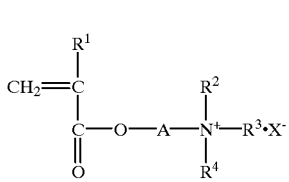

(I)

wherein $R^1$ is H or a methyl group; $R^2$, $R^3$, and $R^4$ are each independently H, an alkyl group, or an aralkyl group; A is an alkylene group; and $X^-$ is a counter anion (2) continuing the polymerization until the polymerization rate exceeds 95%;

(3) purifying the obtained aqueous polymer by ultrafiltration;

(4) concentrating the obtained ultrafiltrated residue by depressurization at a temperature of the solution lower than 100° C.; and (5) drying the obtained concentrated solution after the depressurized concentration at a temperature $D_2$ (° C.) for a time $T_2$ (min.), both parameters satisfying the following mathematical relational expression, until the water content of a resulting cationic polymer reaches 10% by weight or less:

$$300 \geq D_2 \times \text{Log}_{10} T_2$$

where $10 \leq D_2 \leq 100$ $T_2 > 1$.

3. The process according to claim 1, wherein the content of the low molecular weight polymer fraction having a weight average molecular weight of 10,000 in the resulting cationic polymer is 10% by weight or less.

4. The process according to claim 1, wherein the content of the cationic monomer represented by the formula (I) in the resulting cationic polymer is 0.05% by weight or less.

5. The process according to claim 1, wherein the content of a hydrolysis product represented by the following formula (II) in the resulting cationic polymer is 0.05% by weight or less:

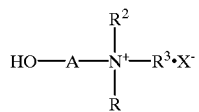

(II)

(wherein A, $R^2$, $R^3$, $R^4$, and X- are the same with A, $R^2$, $R^3$, $R^4$, and $X^-$ in the compound represented by the formula (I)).

6. The process according to claim 1, wherein the content of $R^3X$ in the resulting cationic polymer is 0.05% by weight or less, and $R^3$ and X are the same with $R^3$ and X in the compound represented by the formula (I).

7. The process according to claim 2, wherein the content of the low molecular weight polymer fraction having a weight average molecular weight of 10,000 in the resulting cationic polymer is 10% by weight or less.

8. The process according to claim 2, wherein the content of the cationic monomer represented by the formula (I) in the resulting cationic polymer is 0.05% by weight or less.

9. The process according to claim 2, wherein the content of a hydrolysis product represented by the following formula (II) in the resulting cationic polymer is 0.05% by weight or less:

(wherein A, $R^2$, $R^3$, $R^4$, and $X^-$ are the same with A, $R^2$, $R^4$, and $X^-$ in the compound represented by the formula (I)).

10. The process according to claim 2, wherein the content of $R^3X$ in the resulting cationic polymer is 0.05% by weight or less, and $R^3$ and X are the same with $R^3$ and X in the compound represented by the formula (I).

* * * * *